United States Patent
Padmos et al.

(10) Patent No.: US 12,205,684 B2
(45) Date of Patent: Jan. 21, 2025

(54) SYSTEMS AND METHODS FOR PATIENT-TRIAL MATCHING

(71) Applicant: Flatiron Health, Inc., New York, NY (US)

(72) Inventors: Alexander Padmos, New York, NY (US); Angel Leung, Brooklyn, NY (US); Caroline Nightingale, Brooklyn, NY (US); Zexi Chen, Forest Hills, NY (US); Janet Donegan, Park City, UT (US); Peter Larson, New York, NY (US); Lauren Sutton, New York, NY (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 16/881,317

(22) Filed: May 22, 2020

(65) Prior Publication Data

US 2020/0372979 A1 Nov. 26, 2020

Related U.S. Application Data

(60) Provisional application No. 62/851,870, filed on May 23, 2019.

(51) Int. Cl.
*G16H 10/20* (2018.01)
*G16H 10/60* (2018.01)
*G16H 50/20* (2018.01)

(52) U.S. Cl.
CPC ............ *G16H 10/20* (2018.01); *G16H 10/60* (2018.01); *G16H 50/20* (2018.01)

(58) Field of Classification Search
CPC ........ G16H 10/20; G16H 10/60; G16H 50/20; G16H 15/00
See application file for complete search history.

(56) References Cited

U.S. PATENT DOCUMENTS 10,395,772 B1 *   8/2019   Lucas ................... G16H 10/60
2002/0002325 A1 * 1/2002   Iliff ........................ G16H 50/20
                                                        600/300

(Continued)

FOREIGN PATENT DOCUMENTS

WO    WO-2019/068870 A1    4/2019

OTHER PUBLICATIONS

Susan Jin, et al., "Re-Evaluating Eligibility Criteria for Oncology Clinical Trials: Analysis of Investigational New Drug Applications in 2015" Journal of Clinical Oncology, vol. 35, No. 33, dated Nov. 20, 2017, pp. 3745-3752 (Year: 2017).*

(Continued)

*Primary Examiner* — Gregory D. Moseley
(74) *Attorney, Agent, or Firm* — Wolf, Greenfield & Sacks, P.C.

(57) ABSTRACT

A computer-implemented system for determining trials using a metastatic condition of a patient may include at least one processor programmed to receive a selection of a patient; access, in response to the selection of the patient, a patient dataset associated with the patient; receive a predicted metastatic condition associated with the patient; cause display of at least a first portion of the patient dataset and the predicted metastatic condition; determine, based on at least a second portion of the patient dataset or the predicted metastatic condition, a subset of trials for the patient, wherein the subset of trials for the patient is determined from a plurality of trials; and cause display of at least the subset of the trials for the patient.

16 Claims, 13 Drawing Sheets

(56) References Cited

U.S. PATENT DOCUMENTS

| | | | |
|---|---|---|---|
| 2016/0196441 A1 | 7/2016 | Zhang et al. | |
| 2018/0373496 A1* | 12/2018 | Gschwind | G06F 9/30014 |
| 2019/0059762 A1* | 2/2019 | Starr | A61B 5/316 |
| 2019/0163875 A1* | 5/2019 | Allen | G16H 50/70 |
| 2019/0348178 A1* | 11/2019 | Eleftherou | G16H 50/50 |
| 2020/0243167 A1* | 7/2020 | Will | G06N 5/003 |
| 2020/0265927 A1* | 8/2020 | Clark | G06N 3/084 |

OTHER PUBLICATIONS

Aurelia Bustos et al., "Learning Eligibility in Cancer Clinical Trials using Deep Neural Networks", arxiv.org, Cornell University Library, 201 Olin Library, Cornell University, Ithaca, NY 14853, Mar. 22, 2018, XP081107595, DOI: 10.3390/APP8071206.

PCT Search Report and Written Opinion in International Application No. PCT/US2020/034229 dated Aug. 7, 2020 (14 pages).

\* cited by examiner

| Trial name ▲ | Trial description | Status | Disease | Line of therapy | Metastatic Status |
|---|---|---|---|---|---|
| PA-7471042 | Study Of Drug A27 (PF-00299804)... | Active, Not Recruiting | Breast Cancer | Metastatic: 1st line Metastatic: 2nd line | Metastatic Only ⋮ |
| BRE-1205 | A Phase III Randomized Double-bli... | Closed | Prostate Cancer | None selected | Non-Metastatic Only ⋮ |
| BRE-2252 | A Randomized Phase III Trial of C... | Active, Recruiting | Non-Small Cell Lun... | Adjuvant | Metastatic or Non-Metastatic ⋮ |
| BRE-2321 | Anastrozole in Preventing Breast... | Pending | Breast Cancer | Metastatic: 1st line | Metastatic Only ⋮ |
| CRC-11182 | A Phase II Study of the Combina... | Active, Recruiting | Colon Cancer | Metastatic: 1st line | Metastatic or Non-Metastatic ⋮ |
| CRC0101 | Phase III, multicenter, open-labe... | Active, Recruiting | Colon Cancer Rectal Cancer | Metastatic: 3rd line and beyond | Metastatic or Non-Metastatic ⋮ |
| END-8873 Trial | Efficacy of Drug R94 on Norm... | Pending | Breast Cancer | Metastatic: 1st line Metastatic: 2nd line | Non-Metastatic Only ⋮ |
| GOG3029 | Effect of Tumor Treating Fields... | Pending | Ovarian Cancer Ovarian, Epithelial... Ovarian, Malignant... ... and 1 others | Metastatic: 2nd line | Metastatic Only ⋮ |

Protocol Overview

Study ID

[                                                                    ]

Enter the NCT identifier to retrieve the protocol overview from clinicaltrials.gov.

NCT Identifier

| NCT999000111 | Retrieve Trial Information |

☐ NCT identifier not available

Trial Name *

| 18-223: Jones-Arthur Cancer Institute |

Study Drug

| Drug B670 |

Sponsor

| Jones-Arthur Cancer Institute |

Study Type

| Interventional |

Trial Description *

| B670 + Additive in BRCA Mutant Breast Cancer |

Metastatic Status ⓘ ~ 301

○ Metastatic only    ○ Non-metastatic only    ○ Either Metastatic or Non-metastatic

~ 302

Contract Research Organization

Suggested trials  Show description

Fri, 11/08/2018  < >  | All physicians ▼ | All locations ▼ | Hide viewed appointments | Print

701

Filtered by: None.

| Patient | Diagnosis | Visit Type | Physician | Location | Current status on trial(s) | | |
|---|---|---|---|---|---|---|---|
| ◉ Genelle Larson A056176 | Breast Cancer | Office Visit | Klocko, Dagmar | South Aletha Canc... | END-667 Trial BRE-2321 | ○ In Pre-screening ○ Deemed ineligible | |
| ◉ Ollie X. Stiedemann A023608 | Breast Cancer and 7 others | Office Visit | Barrows, Aurelia | Cancer Specialists... | BRE-2321 REBECCA II: Dar... TEST | ○ Watching ○ In Pre-screening ○ Deemed ineligible | |
| ◉ Christina Weissnat A050336 | Breast Cancer and 3 others | Treatment | | Kellview Cancer S... | REBECCA II: Dani... A7671062: PD-345 BRE-2321 | ◉ Active ○ In Consenting Pr... ○ Deemed ineligible | |

Suggested trials 800

Fri., 11/08/2018 810

Filtered by: None.

| Patient |
|---|
| ⊘ Genelle Larson<br>A056174 |
| ⊘ Ollie X. Stiedeman<br>A023408 |
| ⊘ Christina Weissna<br>A050334 |

---

Ollie X. Stiedemann 821    DOB: 08/25/1969 (50 years old)    [Set reminder] [Mark unviewed] 820 [Close]

Notifications:
10/22/2018: Consider this patient, from L zAltos-Sutton in OncoEMR 822    Sutton

| Patient Clinical Info | [Open OncoEMR Documents] |
|---|---|

Diagnosis

Primary Diagnosis in OncoEMR

Breast Cancer    11/16/2017
Stage IIIA (11/16/2017)    Date of diagnosis

Disease Status ⓘ      Likely
last updated: 09/21/2017

Metastatic disease

⊕ Provide metastatic status for patient matching

---

Trials ⓘ

NSCLC - PDL1 - 32342      Show more ⌄
Active, recruiting

Trials to evaluate (4) Trials in screening (2) Archived trials (15) 823

NSCLC-1234
Active, recruiting
◉ Watching by janedoe@flatiron.com. "Waiting on scan"

Lung Cancer    ⊗     ⎫ 824
Metastatic      ⊘ Likely ⎬
PD-L1           ⎭ 825

CA209-345: ABCDE
Active, recruiting
Not statused

Lung Cancer    ⊗
Metastatic      ⊘ Likely

LUN - 34235
Active, recruiting
Inclusion criteria

Lung Cancer     ⊗        ⎫
Metastatic       ⊘ Likely ⎬ 826
EGFR positive   ⊗        ⎪
BRAF positive    ⊘        ⎪
On Ribolitar      ⊘        ⎭

Hide unknown / not tested criteria

*FIG. 8A*

Suggested trials — 810

Fri., 11/08/2018

Filtered by: None.

| Patient | | |
|---|---|---|
| ⊘ Genelle Larson A056174 | | |
| ⊘ Ollie X. Stiedeman A023408 | | |
| ⊘ Christina Weissna A050334 | | |

---

Verna Frank  [Set reminder] [Mark unviewed] [Close] — 820

Notification:
07/01/18: Document requires signature. Download document, version 2.000.

⊕ Add patient note — 822

Patient Clinical Info  [Open OncoEMR Documents]

Diagnoses
Essential (primary) hypertension  01/21/2014
Non-small cell lung cancer Stage IIa (10/05/16)  11/04/11
Polycythemia vera  09/23/13

Disease Status
Metastatic disease  Likely
  last updated: 09/21/2017
⊕ Provide metastatic status for patient matching

Biomarkers ⓘ
ROS1  02/15/2017: Positive
PD-L1  01/27/2017: Positive
EGFR  02/15/2017: Negative
ALK  02/15/2017: Negative

Drug order history
Ado-yestib pestanine  First Order: 02/01/2017

Trials ⓘ

Active trials

NSCLC - PDL1- 32342 — 823
Active, recruiting
⊕ Add to timeline

○ 08/10/17 — Active
  by janedoe@flatiron.com

○ 07/31/17 — Signed main study consent    [Edit] [Delete]
  by janedoe@flatiron.com ○ 07/29/17 — Marked as consider
  by johnsmith@flatiron.com ○ 07/27/17 — In pre-screening
  by janedoe@flatiron.com
  "patient matches i/e criteria"

○ 07/02/17 — Watching
  by janedoe@flatiron.com
  "Waiting on scan"

Trials to evaluate (4)  Trials in screening (2)  Archived trials (15)

NSCLC-1234
Active, recruiting
◉ Watching by janedoe@flatiron.com. "Waiting on scan"
Lung Cancer Show less ∧
Additional info

[Edit] [Delete]

*FIG. 8B*

SYSTEMS AND METHODS FOR PATIENT-TRIAL MATCHING

CROSS-REFERENCE TO RELATED APPLICATION

This application claims the benefit of priority of U.S. Provisional Patent Application No. 62/851,870, filed May 23, 2019, the contents of which are incorporated herein by reference in their entirety.

BACKGROUND

Technical Field

The present disclosure relates to systems and methods for determining trials using a metastatic condition of a patient.

Background Information

The cancer research community is constantly faced with a challenge of identifying patients who are eligible for clinical trials. There are often many barriers that may prevent a patient from participating in a clinical trial. For example, identifying a patient at just the right time such as, for instance, when they are ready to be put on a therapy but have not yet started one, is often challenging when a practice may have dozens of trials open, each with a dozen or more inclusion and/or exclusion criteria, and with hundreds of patients coming into a practice a day. Further complicating the process is the fact that a metastatic condition of a patient may change drastically from one day to the next, and this change may only be captured in a handwritten note by a physician. This can lead to patients who do have a disqualifying metastatic condition being placed in trials for which they do not qualify, disrupting the results of the trial. Thus, to overcome these challenges faced by existing systems, it is desirable to identify eligible patients for a clinical trial and eligible trials for a patient more efficiently based on metastatic conditions. Additionally, it is desirable to predict a metastatic condition for a patient, to accurately and efficiently coordinate the matching of patients to trials.

SUMMARY

Embodiments consistent with the present disclosure include systems and methods for determining trials using a metastatic condition of a patient. Embodiments of the present disclosure may overcome one or more aspects of existing techniques for determining trials based on computer-generated algorithms according metastatic conditions. The use of computer-generated algorithms in accordance with embodiments of the present disclosure thus allows for faster and more efficient ways for providing patients, physicians, and researchers with reliable suggestions of eligible trials that may benefit the patients.

In an embodiment, a device for determining trials using a metastatic condition of a patient may include at least one processor programmed to: receive a selection of the patient; access, in response to the selection of the patient, a patient dataset associated with the patient; receive a predicted metastatic condition associated with the patient; cause display of at least a first portion of the patient dataset and the predicted metastatic condition; determine, based on at least a second portion of the patient dataset or the predicted metastatic condition, a subset of trials for the patient, wherein the subset of trials for the patient is determined from a plurality of trials; and cause display of at least the subset of the trials for the patient.

In an embodiment, a method for determining trials using a metastatic condition of a patient may include receiving a selection of the patient; accessing, in response to the selection of the patient, a patient dataset associated with the patient; receiving a predicted metastatic condition associated with the patient; causing display of the at least a first portion of the patient dataset and the predicted metastatic condition; determining, based on at least a second portion of the patient dataset or the predicted metastatic condition, a subset of trials for the patient, wherein the subset of trials for the patient is determined from a plurality of trials; and causing display of at least the subset of trials for the patient.

In an embodiment, a non-transitory computer-readable medium may include instructions that when executed by one or more processors, cause the one or more processors to: receive a selection of the patient; access, in response to the selection of the patient, a patient dataset associated with the patient; receive a predicted metastatic condition associated with the patient; cause display of at least a first portion of the patient dataset and the predicted metastatic condition; determine, based on at least a second portion of the patient dataset or the predicted metastatic condition, a subset of trials for the patient, wherein the subset of trials for the patient is determined from a plurality of trials; and cause display of at least the subset of trials for the patient.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 2 is a diagram illustrating an exemplary user interface for viewing trials, consistent with the present disclosure.

FIG. 3 is a diagram illustrating an exemplary user interface for receiving user input for creating a new trial, consistent with the present disclosure.

FIG. 7 is a diagram illustrating an exemplary user interface for providing one or more suggested trials for patients, consistent with the present disclosure.

FIGS. 8A and 8B are diagrams illustrating an exemplary user interface for providing information of a patient and suggested trials, consistent with the present disclosure.

DETAILED DESCRIPTION

Figure 1A:
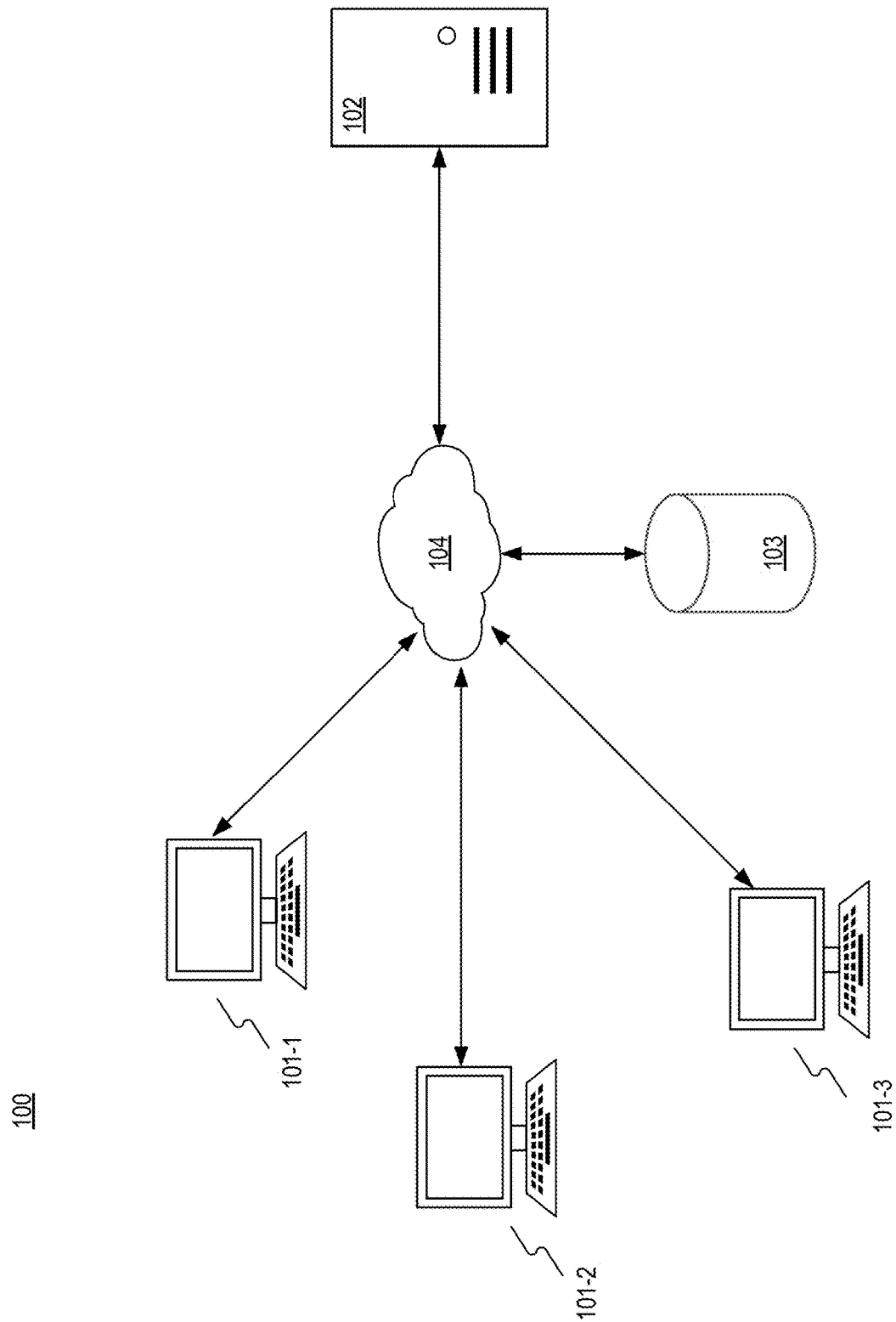
FIG. 1A is a block diagram illustrating an exemplary system for providing one or more suggested patients for a trial, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, non-volatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

In this disclosure, a system for one or more trials is disclosed.

FIG. 1A illustrates an exemplary system 100 for implementing embodiments consistent with the present disclosure, described in detail below. As shown in FIG. 1A, system 100 may include one or more client devices 101, a computing device 102, a database 103, and a network 104. It will be appreciated from this disclosure that the number and arrangement of these components are exemplary and provided for purposes of illustration. Other arrangements and numbers of components may be used without departing from the teachings and embodiments of the present disclosure.

A client device 101 (e.g., client device 101-1, 101-2, 101-3) may be configured to receive user input from a user for creating a new trial. For example, client device 101 may reside at a clinic, and a user (e.g., a physician or administrator) may enter information for creating a new trial portfolio at an input device (such as an input device 153) of client device 101. Client device 101 may include a processor, memory, input device, output device, or other computing component. For example, client device 101 may have components corresponding to those of computing device 102. By way of example, the user may enter an identification number (e.g., a National Clinical Trial (NCT) number or ClinicalTrials.gov identifier) at an interface of client device 101 for creating a new trial, and client device 101 may transmit the identification number to computing device 102. Computing device 102 may create a trial portfolio for the new trial based on the identification number. Client device 101 may also receive and present information received from computing device 102. For example, client device 101 may receive information relating to suggested patients for one or more trials from computing device 102 and present the information at an interface of client device 101 to the user. In some embodiments, client devices 101-1, 101-2, and 101-2 may reside at the same site or different sites.

Computing device 102 may be configured to receive information from client device 101 for creating the new trial portfolio from client device 101. Computing device 102 may also create a trial portfolio based on the information received from computing device 102. The trial information received by computing device 102 may include at least a portion of trial eligibility criteria associated with the trial, such as a metastatic condition eligibility restriction. Computing device 102 may also create a new trial portfolio for the trial based on the trial information. The trial portfolio may include one or more trial eligibility criteria for determining whether a patient is eligible for the trial. For example, the trial eligibility criteria may include a metastatic condition restriction that an eligible patent must have a verified metastatic condition. Computing device 102 may further automatically generate an algorithm for suggesting one or more eligible patients for the new trial based on the trial eligibility criteria. For example, computing device 102 may automatically generate an algorithm representing an expression tree (e.g., expression tree structures 401, 402 illustrated in FIGS. 4A and 4B) based on the trial eligibility criteria, and the nodes and/or leaves of the expression tree may represent the trial eligibility criteria. In some embodiments, a strength of eligibility may be determined, which may be based on a degree to which a patient matches a set of criteria. For example, a patient matching 90% of a set of criteria may have a higher strength of eligibility than a patient matching 50% of a set of criteria. As another example, a patient with a verified metastatic condition of "metastatic" may have a higher strength of eligibility for a trial having an eligibility restriction of a "metastatic" condition than a patient who only has a predicted metastatic condition. In some embodiments, a strength of eligibility may be stored and/or transmitted by a client device 101, a computing device 102, and/or any other device suitable for managing patient data. In some embodiments, a strength of eligibility may be determined for criteria that are designated as preferred but not for criteria designated as absolute restrictions on eligibility.

Computing device 102 may also be configured to obtain electronic medical records associated with a plurality of patients and determine whether one or more patients may be eligible for the new trial based on the algorithm and electronic medical records. For example, computing device 102 may obtain electronic medical records associated with the patients of a clinical (e.g., the clinical associated with client device 101). For example, client device 101 and/or computing device 102 may be configured to receive and/or process input information for a model. For example, client device 101 may include or may be connected to a scanning device, which may scan documents (e.g., documents containing unstructured data) associated with a patient. For example, a scanning device (e.g., a portable document scanner) may scan a handwritten note from a doctor and convert it to an image or other data entity (e.g., structured data). Computing device 102 may determine one or more patients among the patients of the clinical who may be eligible for the new trial based on the algorithm and electronic medical records (e.g., structured or unstructured data). By way of example, computing device 102 may create a namedtuple that has numbers and a series of letters for each of the patients based on the electronic medical record (e.g., age, disease, biomarkers). Computing device 102 may evaluate the created namedtuples associated with the patients against the expression tree, which may return a number indicating the eligibility for each of the patients. For example, the expression-tree algorithm may output "0" for ineligible or "1" for eligible. Alternatively, the algorithm may output a probability value indicating the eligibility for each of the patients.

Computing device 102 may further be configured to output one or more suggested eligible patients for the new trial. For example, computing device 102 may output one or more suggested patients to an output device (e.g., a display, printer). Alternatively or additionally, computing device 102 may transmit instructions for displaying information representing the one or more suggested patients to client device 101, which may present the information to the user.

In some embodiments, computing device 102 may be configured to provide one or more suggested trials for a patient. For example, the user may select a patient via the input device of client device 101 (or computing device 102), and computing device 102 may provide one or more trials for which the patient may be eligible based on one or more patient-trial matching algorithms and the electronic medical record associated with the patient.

In some embodiments, client device 101 and computing device 102 may be integrated into one device configured to perform the functions of client device 101 and computing device 102 disclosed in this application. For example, a user may input information for creating a new trial via input device 153 of computing device 102, which may display one or more suggested patients for the new trial via an output device (e.g., output device 154, discussed below).

Database 103 may be configured to store information and data for one or more components of system 100. For example, database 103 may store electronic medical records associated with one or more patients. Database 103 may also store information relating to one or more trials. For example, database 103 may store trial eligibility criteria associated with each of the trials, such as a metastatic condition criterion. In some embodiments, database 103 may also store patient-trial matching algorithms for determining one or more suggested eligible patients for a trial, and/or one or more suggested eligible trials for a patient. Client device 101 and/or computing device 102 may be configured to access and obtain the data stored on database 103 via network 104. In some embodiments, database 103 may be operated by a third party. For example, computing device 102 may request information relating to a particular trial from database 103, which may transmit the requested information to computing device 102. By way of example, computing device 102 may request the information of trial by transmitting a trial identifier (e.g., an NCT number) to database 103, which may transmit the requested information (e.g., trial eligibility criteria) to computing device 102.

Network 104 may be configured to facilitate communications among the components of system 100. Network 104 may include a local area network (LAN), a wide area network (WAN), portions of the Internet, an Intranet, a cellular network, a short-ranged network (e.g., a Bluetooth™ based network), or the like, or a combination thereof.

Figure 1B:
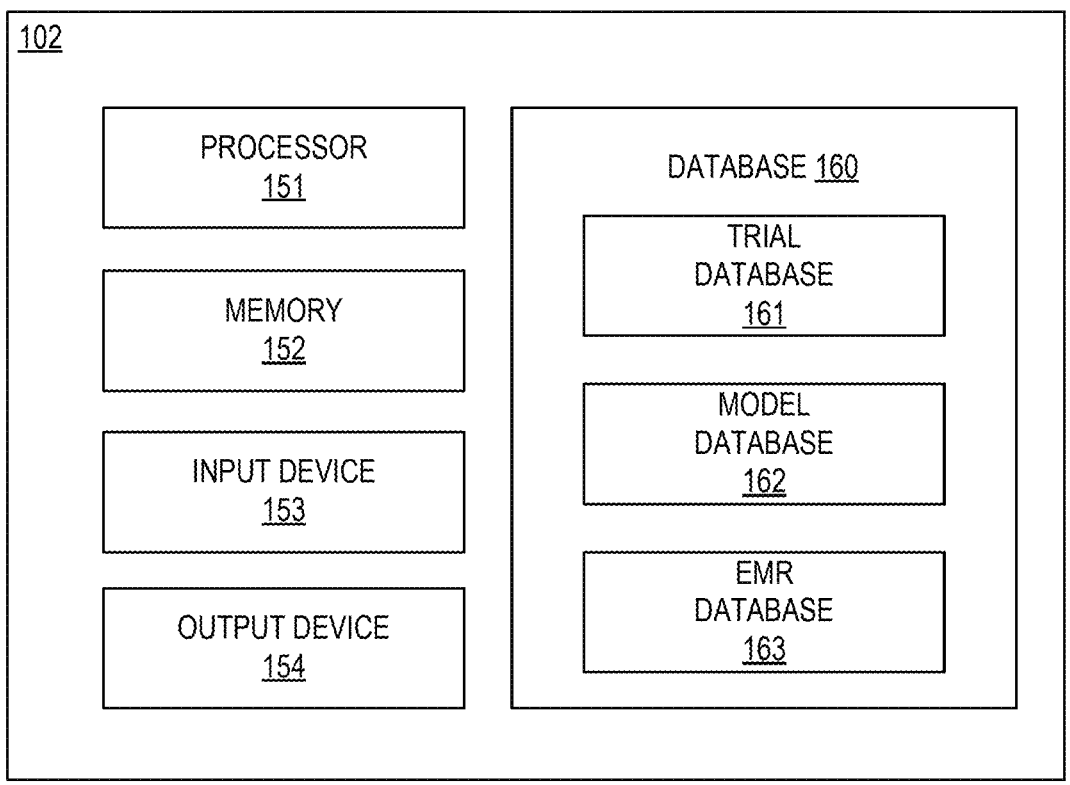
FIG. 1B is a block diagram illustrating an exemplary computing device for providing one or more suggested patients for a trial, consistent with the present disclosure.

FIG. 1B is a block diagram illustrating an exemplary computing device 102. Computing device 102 may include at least one processor (e.g., processor 151), a memory 152, an input device 153, an output device 154, and a database 160.

Processor 151 may be configured to perform one or more functions described in this application. Computing device 102 may also include a memory 152 that may store instructions for various components of computing device 102. For example, memory 152 may store instructions that, when executed by processor 151, may be configured to cause processor 151 to perform one or more functions described herein.

Input device 153 may be configured to receive input from the user of computing device 102, and one or more components of computing device 102 may perform one or more functions in response to the input received. In some embodiments, input device 153 may include a touchscreen, a keyboard, a microphone, a speaker, a haptic device, a camera, a button, a dial, a switch, a knob, a touch pad, a button, a microphone, a location sensor, an accelerometer, a camera, a fingerprint scanner, a retinal scanner, a biometric input device, an ultrasonic scanner, a transceiver, an input device, an output device, or other input device to perform methods of the disclosed embodiments. For example, input device 153 may include an interface displayed on a touchscreen (e.g., output device 154). Output device 154 may be configured to output information and/or data to the user. For example, output device 154 may include a display configured to display one or more suggested patients for a trial. In some embodiments, output device 154 may include a touchscreen.

Database 160 may be configured to store various data and information for one or more components of computing device 102. For example, database 160 may include a trial database 161, a model database 162, and an electronic medical record (EMR) database 163. Trial database 161 may be configured to store information relating to one or more trials. For example, trial database 161 may store a trial portfolio for each of the trials, which may include trial eligibility criteria of a trial. Trial eligibility criteria of a trial may include a trial status, a trial disease, a trial line of therapy, an eligibility age, a trial biomarker criterion, a predicted metastatic condition criterion, a verified metastatic condition criterion, or the like, or a combination thereof. In some embodiments, a trial portfolio may also include trial name, trial description, or the like, or a combination thereof. Trial database 161 may further store edit history including changes made to a trial. Computing device 102 may obtain information relating to the trials from trial database 161 and modify the information if needed. For example, computing device 102 may create a trial portfolio for a new trial and store the trial portfolio into trial database 161.

Model database 162 may store patient-trial matching models or algorithms. A patient-trial matching algorithm refers to an algorithm for determining one or more eligible patients for a trial and/or for determining one or more suggested eligible trials for a patient. Computing device 102 may obtain algorithms from model database 162. In some embodiments, computing device 102 may create an algorithm for a new trial and store the created algorithm into model database 162. EMR database 163 may store electronic medical records associated with patients. Processor 151 may receive one or more electronic medical records from EMR database 163.

FIG. 2 is a diagram illustrating an exemplary user interface 200 for viewing trials, consistent with the present disclosure. User interface 200 may be displayed via output device 154 of computing device 102 (e.g., a display or touchscreen). Alternatively or additionally, computing device 102 may transmit instructions to client device 101 for displaying user interface 200 via an output device of client device 101 (e.g., a display or touchscreen). Computing device 102 may obtain trial data from a database (e.g., database 103, database 160) and render user interface 200 based on the obtained trial data.

User interface 200 may include a trial list 201. Trial list 201 may include trial name, trial description, trial status, trial disease, trial line of therapy, or the like, or a combination thereof. User interface 200 may also include one or more filters 202, such as filters by trial name, trial description, trial status, trial disease, trial line of therapy, or the like, or a combination thereof. In some embodiments, for each trial, user interface 200 may display the edit history, which may include changes made to the trial information by users at the practice. Thus, users may be able to access one location to see all clinical trials across their practice, the trial status, and the disease and line of therapy that the trial is recruiting. This may help users understand where there may be a gap in their trial portfolio and where they may need to open another trial.

User interface 200 may include at least one filter 202 (multiple shown), which may be interacted with by a user to filter the trials in trial list 201. For example, a user may input a search term into a filter 202, and trials associated with (e.g., trials having trial data containing) the search term will be displaying in trial list 201. As another example, filter 202 may comprise a drop-down menu, which may allow a user to select a particular trial status, disease, line of therapy, metastatic condition, etc.

User interface 200 may also include a trial categorical data element 203, which may indicate a trial name, trial description, trial recruitment status, disease, line of therapy, metastatic condition, etc., any of which may be associated with a particular trial. In some embodiments, a trial categorical data element 203 may be selectable by a user for further configuration. For example, selecting a trial categorical data element 203 may cause an interface similar to user interface 300 to be displayed. In some embodiments, only a user with proper privileges may change trial data (e.g., a user that is logged into a privileged account on a client device 101 or a computing device 102).

User interface 204 may also include category indicators 204, which may correspond to a particular type of trial categorical data element 203, and may be interactable by a user. In some embodiments, a category indicator may filter, un-filter, and/or re-order displayed trial information when selected by a user. In some embodiments, a user input at a category indicator may remove categorical data elements 203 that correspond to that category indicator from user interface 204.

User interface 200 may also include a button 205 for adding a new trial. For example, the user may click or select button 205 (e.g., using a data input device or via selection on a touchscreen), and computing device 102 may render another user interface for the user to enter the information relating to the new trial.

FIG. 3 is a diagram illustrating an exemplary user interface 300 for receiving user input for creating a new trial, consistent with the present disclosure. User interface 300 may be displayed via output device 154 of computing device 102 (e.g., a display or touchscreen), and the user may enter information via input device 153. Alternatively or additionally, computing device 102 may transmit instructions to client device 101 for displaying user interface 300 via an output device of client device 101 (e.g., a display or touchscreen) and for receiving user input via an input device of client device 101.

User interface 300 may include one or more input areas (e.g., fields) for the user to enter to add the new trial. For example, the user may enter a trial identification number. Computing device 102 may obtain or generate a trial based on the trial identification number. By way of example, the user may enter an NCT number, and computing device 102 may obtain the trial information from a database or a third party (e.g., clinicaltrials.gov) based on the received NCT number, including, for example, trial name, study drug, sponsor, study type, trial description, diagnosis, biomarker criteria, line of therapy, or the like, or a combination thereof. Computing device 102 may also populate the information obtained in user interface 300 accordingly (e.g., automatically). In some embodiments, the user may enter at least a portion of the trial information manually. For example, if an NCT number is not available, the user may check a box to indicate such. User interface 300 may prompt the user to manually complete these input areas.

In some embodiments, the trial information may include site information identifying a location where the new trial is to be conducted. For example, the user may enter site information that may help medical practices have oversight into the operations at their practice and receive reporting on their trial performance. Operational data areas may include site ID, principal investigator, trial status, enrollment initiation date, enrollment closing date, institutional review board (IRB) approval date, site initiation visit date, contract execution date, number of days for data entry, enrollment goal (e.g., the number of patients), links to external sources, or the like, or a combination thereof.

Computing device 102 may create a trial portfolio for the new trial store the trial information in database 103 and/or database 160. The trial portfolio may include trial eligibility criteria of the trial (e.g., a metastatic condition). A potential benefit of this approach may be that the user of the system (e.g., an administrator, physician, research coordinator) is able to determine eligible patients at the practice (e.g., a clinical site) against the eligibility criteria. Additionally, the system can provide the user with operational reporting on the trials and patients. This approach may significantly reduce the number of patients that the user needs to review for potential trial eligibility, thereby improving trial recruitment for the practice as the user is spending more time on reviewing patients with a higher likelihood of eligibility.

Computing device 102 may be configured to determine one or more suggested eligible patients for the new trial. For example, computing device 102 may create a patient-trial matching algorithm for determining one or more eligible patients for the new trial based on trial eligibility criteria of the trial. Computing device 102 may also obtain electronic medical records associated with a plurality of patients. For example, computing device 102 may obtain electronic medical records associated with the patients at one or more clinical sites where client device 101 and/or computing device 102 operate from a database (e.g., database 103, database 160). Computing device 102 may further determine one or more eligible patients for the trial based on the electronic medical records and algorithm.

Solely by way of example, the trial eligibility criteria for an example trial may include the following criteria:
1. Is the patient over 18? If yes, go to step 2. If not, they are not eligible.
2. Does the patient have breast cancer? If yes, go to step 3. If not, go to step 4.
3. Is the patient estrogen receptor negative (ER-) and progesterone receptor negative (PR-)? If yes, they are eligible. If not, they are not.
4. Does the patient have colorectal cancer? If yes, go to step 5. If not, they are not eligible.
5. Does the patient have a gene Kirsten rat sarcoma viral oncogene homolog (KRAS) mutation? If yes, they are eligible. If not, they are not.

Figure 4A:
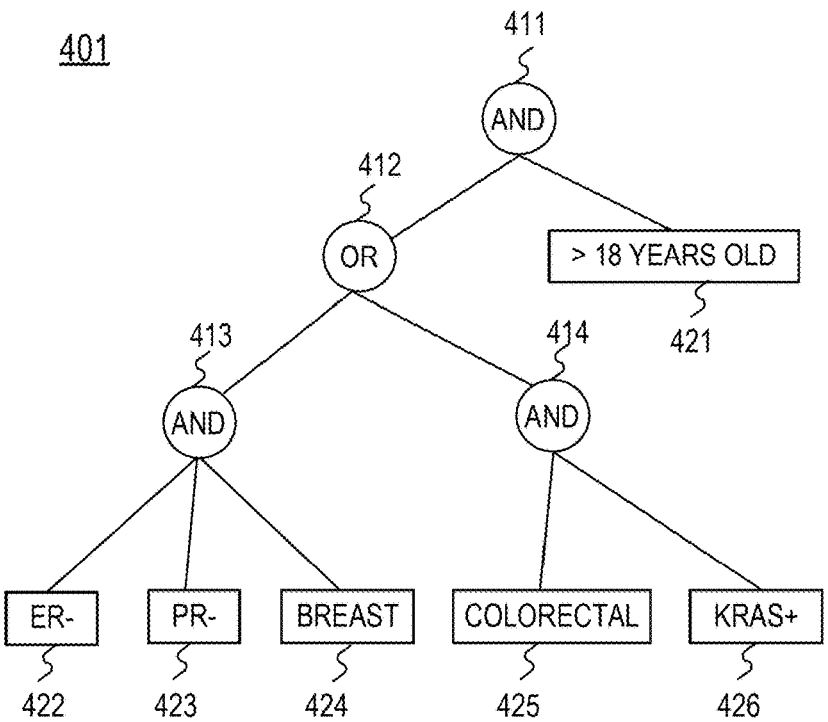
FIGS. 4A and 4B are diagrams illustrating exemplary expression tree structures for one or more suggested patients for a trial, consistent with the present disclosure.

The above trial eligibility criteria may be represented with Boolean operators, as follows:

(Age>18) AND (ER=Negative AND PR=Negative AND Disease=Breast) OR (KRAS=Positive AND Disease=Colorectal), which may be represented as an exemplary expression tree 401 illustrated in FIG. 4A.

As shown in FIG. 4A, expression tree 401 may include operators 411, 412, 413, and 414, and criteria elements 421, 422, 423, 424, 425, and 426. For example, element 412 may represent that the patient must be over 18 years old. As another example, operators 413 and 414, and elements 422-426 represent that the patient must be either (1) ER negative and PR negative and having breast cancer, or (2) having colorectal cancer and KRAS positive. When computing device 102 evaluates each node, computing device 102 may bubble up the result to the node above it and obtain a result of whether a patient is eligible for this trial. For example, for a patient who has breast cancer and is ER- and PR-, but does not have colorectal cancer and hasn't tested KRAS+ may be eligible for the trial because of the left subtree of express tree 401.

In some embodiments, each leaf node in the expression tree represents a single inclusion or exclusion criterion. The nodes (and their criteria) may be mixed and matched into different trees to form the criteria for different trials. Each leaf node may have a role in determining whether a patient is eligible, e.g., taking a patient's clinical information as its input and returning a value that may affect the eligibility as an output. Using an expression tree, the system may enable the user to visualize the matching criteria for a trial and may query various data sources (e.g., electronic medical records of the patients) through a unified interface.

Figure 4B:
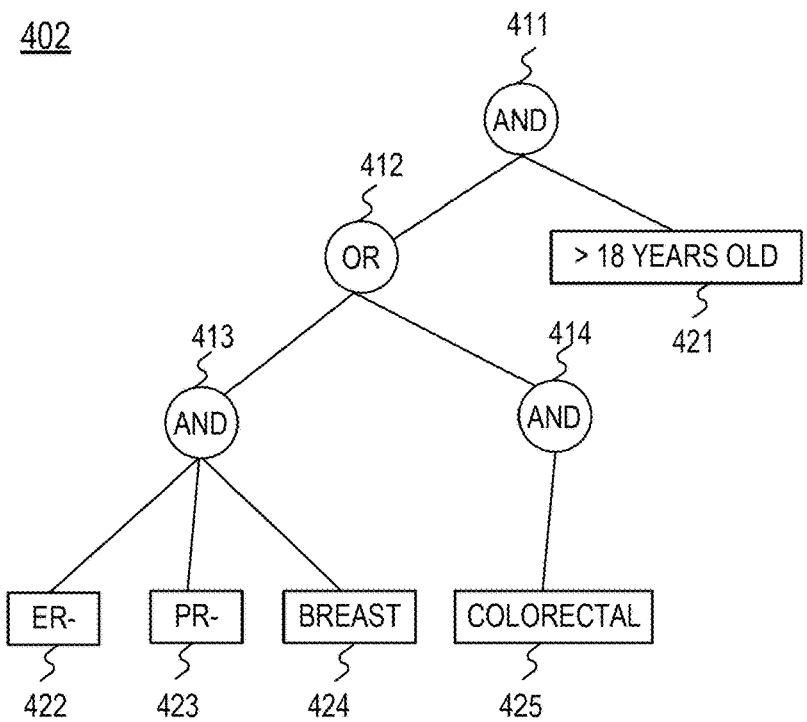

In some embodiments, computing device 102 may be configured to receive updated patient eligibility criteria for the trial. Computing device 102 may also update the patient-trial matching algorithm based on the updated patient eligibility criteria and determine at least one new suggested patient for the updated new trial based on the updated patient-trial matching algorithm and the electronic patient medical records. For example, the user may update the trial eligibility criteria of the trial, and computing device 102 may automatically update the expression tree and patient-trial matching algorithm. As another example, computing device 102 may receive updated trial eligibility criteria from an external database and automatically update the algorithm for the trial based on the updated trial eligibility criteria. By way of example, computing device 102 may receive a user input from the user to delete the KRAS criterium. Computing device 102 may update expression tree 401 by removing leaf node 426 into express tree 402 as illustrated in FIG. 4B. Similarly, if the user adds a new criterium, computing device 102 may insert a new leaf node into the expression tree at an appropriate location. Alternatively or additionally, computing device 102 may modify a leaf node based on input from the user or the system.

Figure 5:
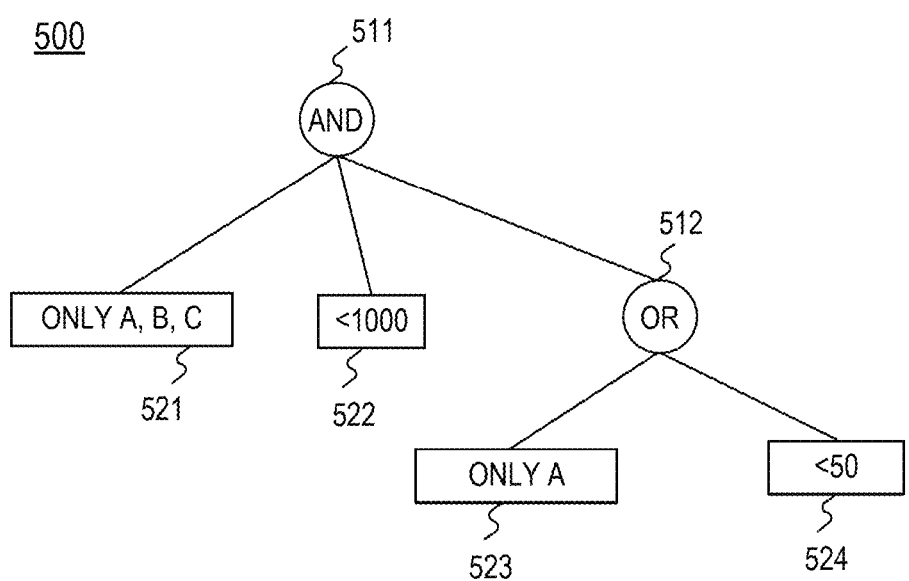
FIG. 5 is a diagram illustrating exemplary expression tree structure for one or more suggested patients for a trial, consistent with the present disclosure.

FIG. 5 is a diagram illustrating an exemplary (simplified) expression tree structure, consistent with the present disclosure. FIG. 5 provides an example to further illustrate an expression tree and algorithm. Expression tree 500 may represent trial eligibility criteria including:

(only A, B, C) AND (<1000) AND (only A OR <50).

Expression tree 500 may include operator nodes 511 and 512, which are two operator classes (AND and OR). Operator classes may include children added as leaf classes (e.g., leaves 521, 522, 523, and 524).

Computing device 102 may automatically generate an algorithm representing expression tree 500 based on the trial eligibility criteria. Exemplary code of the algorithm is shown below.

```
class OrMatchOperator( ):
    def init__(self):
        self.children = [ ]
def match(self, patient):
    prob__no__match = 1.0
    for child in self.children:
        prob__no__match *=float(1 – child.match(patient))
    return 1 - prob__no__match
class AndMatchOperator( ):
    def init__(self):
        self.children = [ ]
def match(self, patient):
    prob__match = 1.0
    for child in self.children:
        prob__match *=float(child.match(patient))
    return prob__match
# Mock leaf node that sees whether a MockClass has only certain letters
# in its 'letters' attribute class LetterMatchLeaf( ):
        def init__(self, allowable__letters):
            self.allowable__letters = allowable__letters
        def match(self, patient):
            if set(patient.letters) – set(self.allowable__letters):
                return 0
            return 1
```

```
# Mock leaf node that sees whether a MockClass has a number
# less than a max_number class NumberMatchLeaf( ):
    def init_(self, max_number):
        self.max_number = max_number
    def match(self, patient):
    return int(patient.number <= self.max_number)
from collections import namedtuple
MockClass = namedtuple('MockClass', ['number', 'letters'])
tree = AndMatchOperator( )
tree.children.append(LetterMatchLeaf(['A', 'B', 'C']))
tree.children.append(NumberMatchLeaf(1000))
subtree = OrMatchOperator( )
subtree.children.append(NumberMatchLeaf(50))
subtree.children.append(LetterMatchLeaf(['A']))
tree.children.append(subtree)
print('Match! (50, [C])') print(tree.match(MockClass(50, ['C']))) print('Match! (50, [A])')
print(tree.match(MockClass(55, ['A'])))
print('Fits neither attribute in the subtree. No match. (50, [C])')
print(tree.match(MockClass(55, ['C'])))
print('Number is too big for the top-level number constraint. No match. (1005, [A])')
print(tree.match(MockClass(1005, ['A'])))
```

The above exemplary code may represent expression tree 500 including trial eligibility criteria. Computing device 102 may also generate a MockClass for each of the patients, which may be a namedtuple that has a number and a series of letters. For example, computing device 102 may create a namedtuple based on the electronic medical record associated with a patient. The codes also include a leaf class, LetterMatchLeaf, which may only allow a certain subset of letters, and another leaf class, NumberMatchLeaf, which may only allow numbers less than a certain number. One having ordinary skills in the art would understand that these classes are only for illustration purposes and other types of classes may also be used for the algorithm. For example, the algorithm may include a leaf class DiseaseMatchLeaf for disease match and a leaf class BiomarkerMatchLeaf for biomarker match.

Computing device 102 may evaluate different MockClass objects (i.e., the patients) against expression tree 500 using the algorithm, which may return 1 (eligible) or 0 (illegible). In some embodiments, a patient-trial matching algorithm may output a probability, and computing device 102 may determine whether a patient is eligible for the trial based on the probability (e.g., the probability exceeding a threshold).

In some embodiments, computing device 102 may obtain or generate a machine learning algorithm for determining one or more suggested eligible patients for the trial based on the trial eligibility criteria. For example, computing device 102 may access a neural network for determining one or more suggested eligible patients for the trial.

Figure 6:
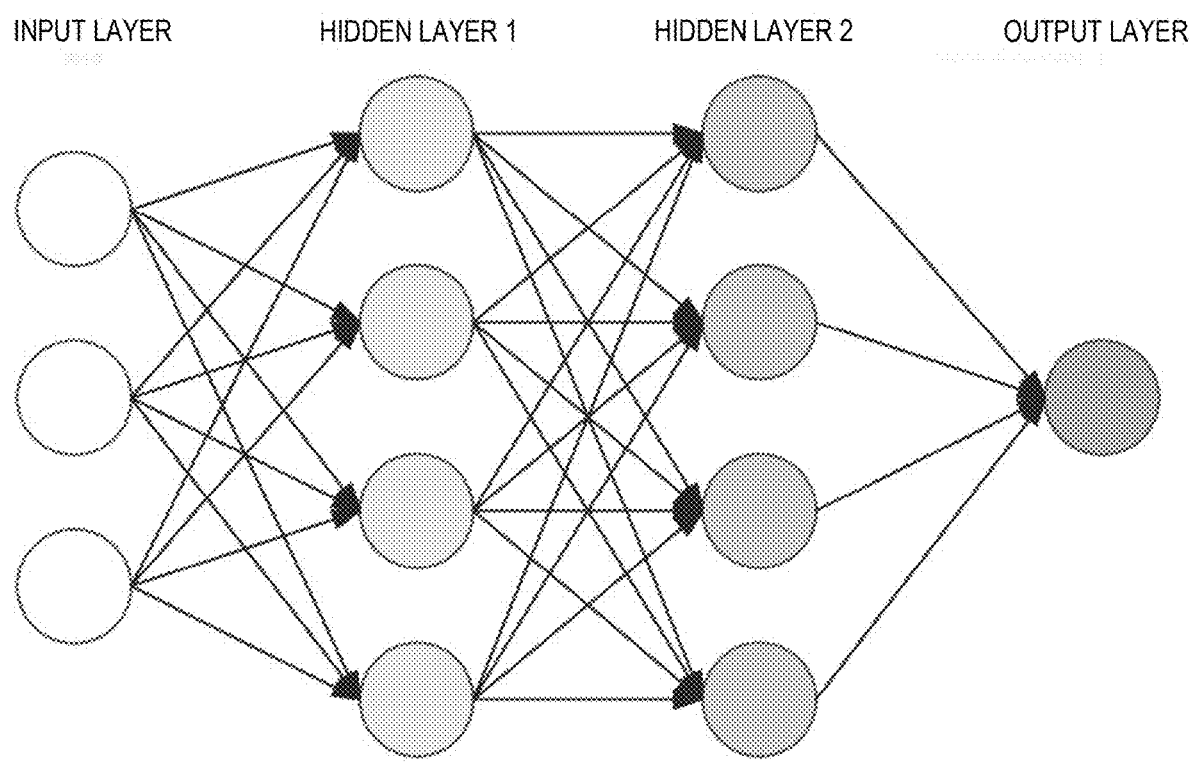
FIG. 6 is a diagram illustrating an exemplary neural network for providing one or more suggested patients for a trial, consistent with the present disclosure.

FIG. 6 illustrates an exemplary neural network 600. Neural network 600 may include an input layer, one or more hidden layers, and an output layer. Each of the layers may include one or more nodes. In some embodiments, the output layer may include one node. Alternatively, the output layer may include a plurality of nodes, and each of the nodes may output data. The input layer may be configured to receive input (e.g., an electronic medical record associated with a patient). In some embodiments, every node in one layer is connected to every other node in the next layer. A node may take the weighted sum of its inputs and pass the weighted sum through a non-linear activation function, the results of which may be output as the input of another node in the next layer. The data may flow from left to right, and the final output may be calculated at the output layer based on the calculation of all the nodes. Neural network 600 may output a probability indicating eligibility of the patient for the trial, which may be based on information from a received input.

In some embodiments, computing device 102 may determine a patient-trial match between a plurality of patients and a plurality of trials, based on the patient-trial matching algorithms associated with the trials and electronic medical records of the patients. For example, computing device 102 may determine one or more suggested eligible patients for each of the trials and/or one or more suggested eligible trials for each of the patients. Computing device 102 may also generate a data structure representing the relationship between the patients and trials and store the data structure in a database (e.g., database 103, database 160). Computing device 102 may further present the data representing the relationship between the patients and trials to the user. For example, computing device 102 may be configured to generate a patient-trial matching report. By way of example, computing device 102 may receive user input for defining filters for the data to appear on the report, including, for example, patient information (e.g., gender, age, location, patient schedule, diagnosis, biomarker, predicted metastatic condition, verified metastatic condition, or the like, or a combination thereof), treatment information (e.g., treatment, inclusionary and/or exclusion drug), and trial information (trial name, study drug, sponsor, study type, trial description, diagnosis, biomarker criteria, line of therapy, or the like, or a combination thereof). Computing device 102 may compile the patients and/or trials that match the filtered data into a report.

FIG. 7 is a diagram illustrating an exemplary user interface for providing one or more suggested trials for patients, consistent with the present disclosure. User interface 700 may be displayed via output device 154 of computing device 102 (e.g., a display or touchscreen), and the user may enter information via input device 153. Alternatively or additionally, computing device 102 may transmit instructions to client device 101 for displaying user interface 700 via an output device of client device 101 (e.g., a display or touchscreen) and for receiving user input via an input device of client device 101.

The user may select a patient schedule, and computing device 102 may access the patient schedule and determine the patients who have been scheduled for a visit according to the patient schedule. For example, the user may select a date (e.g., Nov. 8, 2018 shown in FIG. 700), and computing device 102 may access a patient schedule and determine the patients who have been scheduled for a visit on that date. Alternatively or additionally, the user may view a patient schedule for a period (e.g., a week, a month). Computing device 102 may also provide the user with an interface that shows information relating to the patients and visits. For example, as illustrated in FIG. 7, user interface 700 may include the patients' names, diagnoses, visit types (e.g., office visit, treatment), physicians who the patients visit, locations of the visits, or the like, or a combination thereof.

Computing device 102 may further determine one or more suggested trials for the patients based on the algorithm associated with the trials and the electronic medical records of the patients as described elsewhere in this disclosure. Computing device 102 may also represent user interface 700 to the user, including a list of suggested trials for the patients. As illustrated in FIG. 7, user interface 700 may include a patient list 701, which may include the information of the patients, such as each patient's name, diagnosis, visit type, trial, patient's condition, or the like, or a combination thereof. User interface 700 may also include filters 702 configured to receive the user's input to filter patients and/or trials according to, for example, physician, location, patient diagnosis, visit type, trials, patient status, or the like, or a combination thereof. By presenting suggested trials for the patients who have been scheduled for a visit, the patient-trial matching may be tied directly to the patient schedule of the practice (e.g., a clinical) so that the user of the system can identify eligible patients who are visiting the clinical on a particular date and can schedule meetings with these patients to discuss a potential opportunity to participate in the trials. This may improve the patient recruitment. For example, computing device 102 may provide the user with one or more suggested eligible patients who will visit a clinic on a particular date. As another example, the user may filter the trials and/or patents according to diseases, type of trials, or the like, or a combination thereof. Computing device 102 may inform the physician and/or research coordinator to discuss with the patient about the trial in which the patient may be eligible for participation. For example, computing device 102 may include the trial information into the patient's medical record so that the physician may be reminded when discussing with the patient.

In some embodiments, user interface 700 may display a patient schedule including a doctor appointment of at least one suggested patient. Alternatively or additionally, user interface 700 may display information of a doctor or a location associated with the doctor appointment of the patient.

In some embodiments, computing device 102 may update user interface 700 according to the user's input. For example, if a patient name or patient record has been selected (e.g., clicked into), user interface 700 may show that the patient name or patient record appears as "viewed" (e.g., displaying a "viewed" icon by the name of the patient or by another patient identifier). User interface 700 may include a filter to filter the patient(s) who have been viewed.

In some embodiments, user interface 700 may also include different views according to the user's preferences. For example, user interface 700 may include a "Suggested Trials" view, as shown in FIG. 7, which may display the patients with suggested trials (e.g., actively recruiting or pending trials that match the patient(s)'s diagnosis and biomarkers). Alternatively or additionally, user interface 700 may include a "New Patients" view (not shown), which may display patients who are new to the practice and are having their first visit to the practice. Alternatively or additionally, user interface 700 may include a "Recent Updates" view, which may display patients with suggested trials or who were previously marked as "candidate" or "watching" and should be considered (or reconsidered) now because of a recent scan or pathology report. As another example, recent updates may include a recent scan such as, for example, a pathology or scan report received or a scan order created in the electronic health record associated with a patient since his or her last office visit.

In some embodiments, when the user clicks or selects a patient name in user interface 700, computing device 102 may process the input and provide another user interface for displaying the information of the patient to the user. For example, FIGS. 8A and 8B are diagrams illustrating an exemplary user interface 800 for providing information of a patient and suggested trials, consistent with the present disclosure. User interface 800 may be displayed via output device 154 of computing device 102 (e.g., a display or touchscreen), and the user may enter information via input device 153. Alternatively or additionally, computing device 102 may transmit instructions to client device 101 for displaying user interface 800 via an output device of client device 101 (e.g., a display or touchscreen) and for receiving user input via an input device of client device 101.

As illustrated in FIG. 8A, a user may click or select the patient "Ollie X. Sitedemann" in user interface layout 810 (which is similar to user interface 700). Computing device 102 may provide the user with a user interface layout 820, which may partially overlap with user interface layout 810, for displaying the information of the patient. By way of example, user interface layout 820 may include a region 821, which may display notifications related to a patient and/or trial. Notifications may include, but are not limited to, new trials available for which a patient is eligible, trials for which a patient is no longer eligible, changes to patient information, changes to trial eligibility criteria, and/or a user note.

User interface layout 820 may also include a region 822 displaying the clinical information of the patient, including, for example, patient's diagnosis information, last office visit, disease, or the like, or a combination thereof. In some embodiments, user interface layout 820 may allow the user to open the electronic medical record of the patient. In some embodiments, region 822 may include a disease condition sub-region, described further with respect to FIGS. 8C-8E.

User interface layout 820 may also include a region 823 displaying one or more suggested and/or existing trials for the patient, which may include the trial information, such as trial name, trial description, trial status, trial disease, trial line of therapy, or the like, or a combination thereof. In some embodiments, user interface 800 may display information associated with two or more trials, which may include the statuses of the trials. For example, trials may be sorted into different groups based on a trial status (e.g., an archived status, an in-screening status, an unevaluated status, etc.). In some embodiments, region 823 may display criteria related to trial criteria, which may have corresponding positive eligibility indicators 824, predicted eligibility indicators 825, and/or negative eligibility indicators 826 for a patient. Eligibility indicators may include a combination of shapes, colors, text, animations, and the like, which may indicate different eligibility statuses to a user. By way of example, a positive eligibility indicator 824 may include a bold green circle, which may indicate that a patient meets a particular eligibility criterion. As another example, a negative eligibility indicator 826 may include a bold red circle, which may indicate that a patient does not meet a particular eligibility criterion. In some embodiments, a patient may be predicted to meet an eligibility criterion. For example, based on a computer model, medical record, medical document, or the like, consistent with disclosed embodiments, a predicted eligibility status may be determined, which may be displayed as a predicted eligibility indicator 825. By way of example, if a patient has a predicted metastatic condition that matches a metastatic condition criterion of a trial, a light green circle may be displayed as a predicted eligibility indicator 825. Predicted eligibility indicators 825, like any eligibility indicator, may include text to assist a user in determining details about an eligibility criterion. For example, a predicted eligibility indicator 825 may include text describing a level of confidence of a predicted metastatic condition. In some embodiments, particular predicted eligibility indicators 825 may be associated with certain levels of confidence. For example, if a predicted level of confidence reaches a threshold level (e.g., a 60% chance that patient has a metastatic condition of "metastatic"), a particular indicator may be displayed (e.g., a yellow circle). Other aspects of predicted metastatic conditions are described with respect to other techniques described herein.

The above has been described as examples, as a multitude of combinations of colors, shapes, text, animations, and other visual features may be used to display informative eligibility indicators.

In some embodiments, user interface 800 may present more detailed information regarding a trial. For example, the user may select a trial named "NSCLC-1234" in region 823, and computing device 102 may update region 823 of user interface 800 for displaying more information of the trial, as illustrated in FIG. 8B. For example, region 823 may be updated to display a trial timeline of the trial.

Exemplary FIG. 8B illustrates information that may be displayed related to trials. In some embodiments, region 823 may include a timeline with interactable elements. For example, a timeline may include a number of medical events associated with a patient, which a user may select. In some embodiments, interactable options (e.g., edit, delete, add) may be displayed, which may allow a user to edit, delete, and/or add information (e.g., elements) to a timeline. In some embodiments, some interactable options may only be displayed after an element on a timeline has been selected (e.g., edit, delete).

In some embodiments, user interface 800 may allow the user to take an action on the information of patient and/or one or more of the trials. For example, user interface 800 may allow a user to update the information (e.g., marking the patient as unviewed, marking a trial as viewed, etc.). The updated information may be displayed on user interface 800 accordingly. In some embodiments, the updated information may be saved for further use and/or be made available for another user of the system. For example, when a first user has viewed a patient (by, for example, clicking or selecting in user interface 800), computer device 102 may label the patient as "viewed." Computing device 102 may also provide a second user with a user interface including an indicator indicating that this patient has been viewed. Alternatively or additionally, user interface 800 may allow the user to set up a reminder for the user, physician, or research coordinator, or the like, or a combination thereof, to visit the information. By way of example, user interface 800 may allow the user to create a reminder for a physician who has been scheduled to see the patient to look into potentially eligible trials.

Figure 8C:
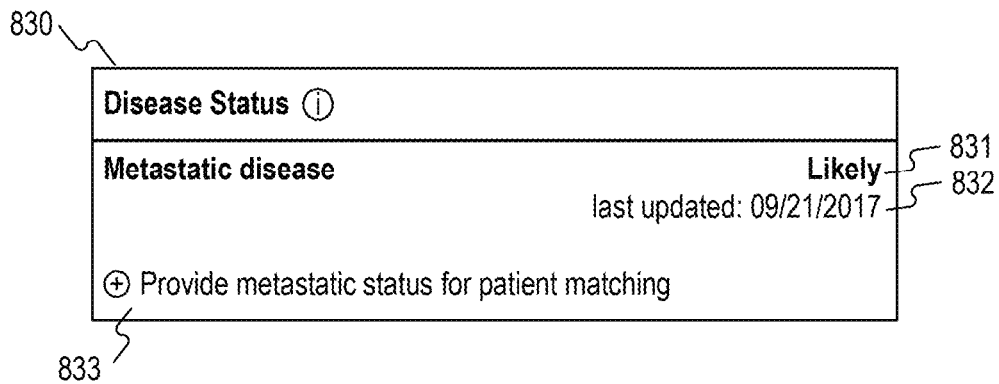
FIGS. 8C, 8D, and 8E are diagrams illustrating exemplary user interfaces for providing management of metastatic conditions.
Figure 8D:
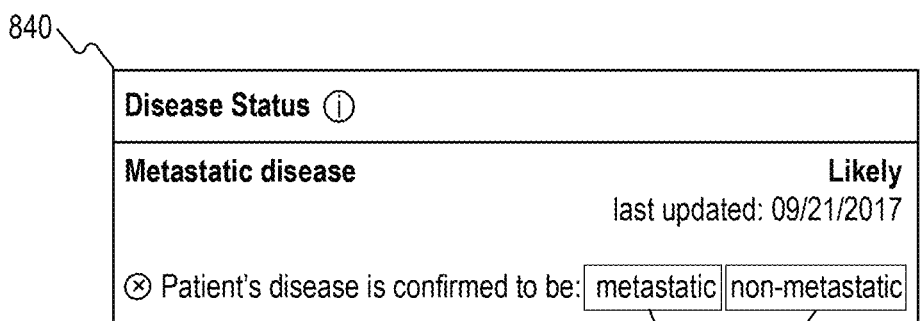
Figure 8E:
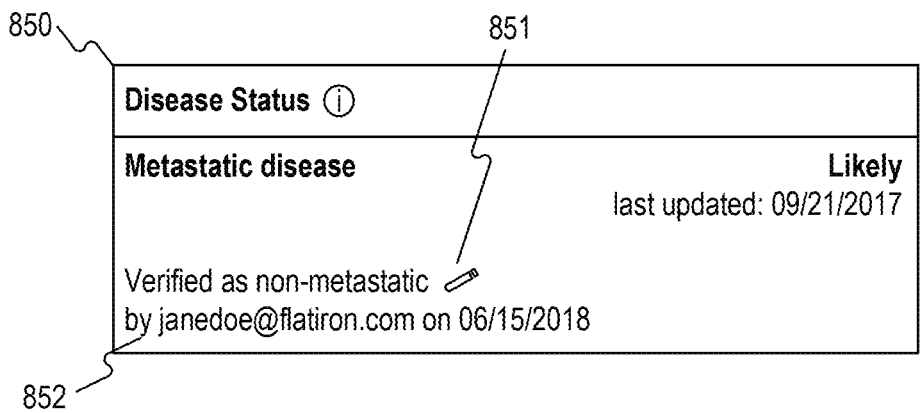

FIGS. 8C, 8D, and 8E illustrate exemplary user interfaces for providing management of metastatic conditions. In some embodiments, sub-region 830 may be displayed after a metastatic condition has been predicted for a patient, consistent with disclosed embodiments. Sub-region 830 may include a prediction level indicator 831, which may correspond to a predicted eligibility indicator 825. For example, prediction level indicator 831 may indicate a level of confidence that a patient has a particular metastatic condition. In some embodiments, sub-region 830 may include an update status indicator 832, which may display a date and/or time at which information associated with a metastatic condition (e.g., metastatic condition, level of confidence, verified condition, etc.) was last updated. Sub-region 830 may also include an interactable verification initiator 833, which may allow a user to verify a metastatic condition. For example, verification initiator 833 may be selectable by a user, and may update sub-region 830 to sub-region 840 upon selection.

Sub-region 840 may include a metastatic condition element 841 and a non-metastatic condition element 842. In some embodiments, selection of a metastatic condition element 841 may verify a patient's metastatic condition (which may have previously been only predicted) as metastatic. In some embodiments, selection of a non-metastatic condition element 842 may verify a patient's metastatic condition (which may have previously been only predicted) as non-metastatic. Verifying a metastatic condition may include updating patient data, trial data, and/or user interfaces, consistent with disclosed embodiments. For example, selection of metastatic condition element 841 or non-metastatic condition element 842 may cause sub-region 840 to update to sub-region 850.

Sub-region 850 may include an interactable verification confirmation indicator 851, which may display a verified metastatic condition. In some embodiments, verification confirmation indicator 851 may be selectable by a user, which may allow a user to change a current verified metastatic condition of a patient. In some embodiments, sub-region 850 may also include a history indicator 852, which may display information associated with a previous change to a metastatic condition. For example, history indicator 852 may display a user who last modified (e.g., verified) a metastatic condition, a time at which a metastatic condition was last changed, a date at which a metastatic condition was last changed., etc.

Figure 9:
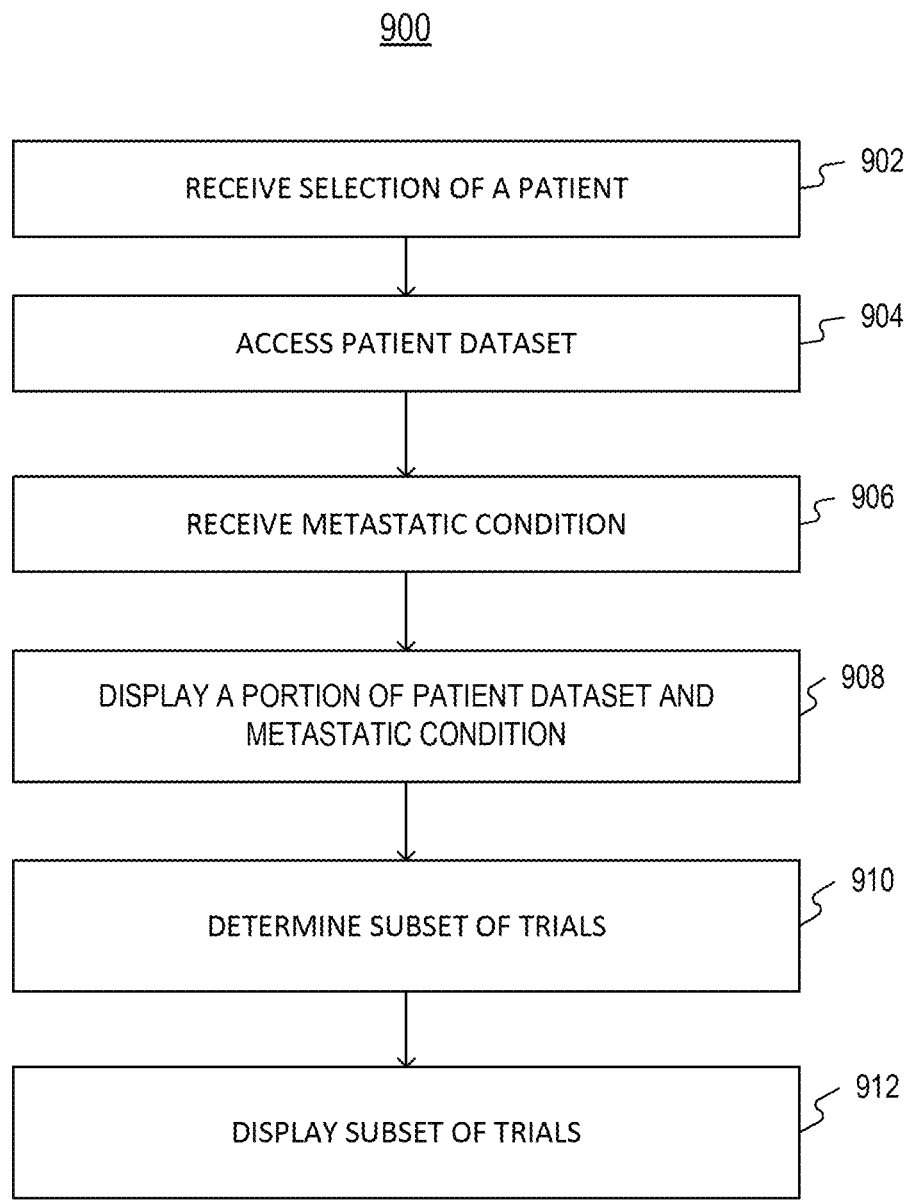
FIG. 9 is a flowchart illustrating an exemplary process for providing one or more suggested patients for a trial, consistent with the present disclosure.

FIG. 9 is a flowchart illustrating an exemplary process 900 for providing one or more suggested patients for a trial, consistent with the present disclosure. While process 900 is described in connection with client device 101, one skilled in the art would understand that one or more steps of process 900 may be performed by other components of the system (e.g., computing device 102 or processor 151).

At step 902, client device 101 may receive a selection of a patient. For example, client device 101 may receive a user input via a user interface of client device 101 for selecting a patient. By way of example, the user may select a patient from a list of patients (e.g., within user interface 700). In some embodiments, a user may search for a patient within a search interface (e.g., using a patient name, patient date of birth, unique patient identifier, etc.) prior to selecting a patient.

At step 904, client device 101 may access a patient dataset. In some embodiments, client device 101 may access a patient dataset in response to a selection of the patient (e.g., at step 901). For example, an accessed patient dataset may be associated with a selected patient. Accessing a patient dataset may include retrieving a patient dataset from a database (e.g., database 103). In some embodiments, a patient dataset may be stored among a plurality of patient datasets at a database. By way of further example, client device 101 may send a request to retrieve a patient dataset from database 103 to computing device 102. In some embodiments, a request to retrieve a patient dataset may be formatted to include a unique patient identifier or other information enabling computing device 102 to distinguish the requested patient dataset from among those stored at database 103.

At step 906, client device 101 may receive a metastatic condition. In some embodiments, a received metastatic condition may be verified metastatic condition or a predicted metastatic condition of a patient. In some embodiments, a metastatic condition may be associated with a patient (e.g., a patient selected at step 902). A predicted metastatic condition may have been predicted by a trained model configured to receive a document, which may include unstructured information. For example, computing device 102 may have received a document (e.g., from a client device 101, which may or may not be the same device performing a step of process 900), and may have applied a trained model to the document to extract information from the document and/or convert the document into a format having structured information. In some embodiments, a predicted metastatic condition may include a degree of likelihood determined by the machine learning model. Steps related to determining and/or updating metastatic statuses are described further with respect to process 1000.

At step 908, client device 101 or computing device 102 may cause display of at least a portion of the patient dataset and a metastatic condition (e.g., a predicted metastatic condition). For example, displayed portions may be displayed within a user interface (e.g., user interface 800), consistent with disclosed embodiments. In some embodiments, the displayed portions may include a subset or entirety of the patient dataset accessed at step 902 and/or the metastatic condition received at step 906.

At step 910, client device 101 may determine a subset of trials for a patient. In some embodiments, determining a subset of trials for a patient may be based on at least a portion of the patient dataset or a metastatic condition (which may or may not be a same portion as of that in step 908). For example, a subset of trials may be determined based on a predicted or verified metastatic condition. By way of example, a first subset of trials may be determined based on a predicted metastatic condition at a first time, and a second subset of trials may be determined based on a verified metastatic condition at a second time. In some embodiments, a subset of trials for a patient may be determined from a plurality of trials. By way of example, computing device 102 may use a patient dataset and/or metastatic condition to determine, from among a set of trials (e.g., stored at a database 103), trials for a subset. In some embodiments, a set of trials may be associated with a metastatic condition criterion (e.g., at least one metastatic condition criterion may be associated with each trial of the set), which may be used in determining a subset of trials. For example, client device 101 may compare a metastatic condition (e.g., a predicted metastatic condition) with a metastatic condition criterion of a trial. In some embodiments, client device 101 may determine that the predicted metastatic condition satisfies the metastatic condition criterion of a trial (e.g., based on the comparison, client device 101 may determine that the predicted metastatic condition matches the metastatic condition criterion), and may then include that trial in the subset of trials, based on this determination. In some embodiments, client device 101 may determine that the predicted metastatic condition does not satisfy the metastatic condition criterion of a trial (e.g., based on the comparison, client device 101 determines that the predicted metastatic condition does not match the metastatic condition criterion), and may then exclude that trial from the subset of trials, based on this determination.

At step 912, client device 101 may cause a display (e.g., at a display of client device 101) of a subset of trials for a patient (e.g., a subset determined at step 910). In some embodiments, computing device 102 may cause the display of a subset of trials for a patient at a client device 101. In some embodiments, causing display of a subset of trials may include displaying criteria of the subset of trials and indicators of a patient qualification status for the criteria (e.g., as shown in exemplary region 823). As described with respect to other figures, displaying a subset of trials may include displaying at least one indicator, interactable element, etc., which may change dynamically based on updates to a patient dataset, a metastatic condition, trial criteria, and the like.

Figure 10:
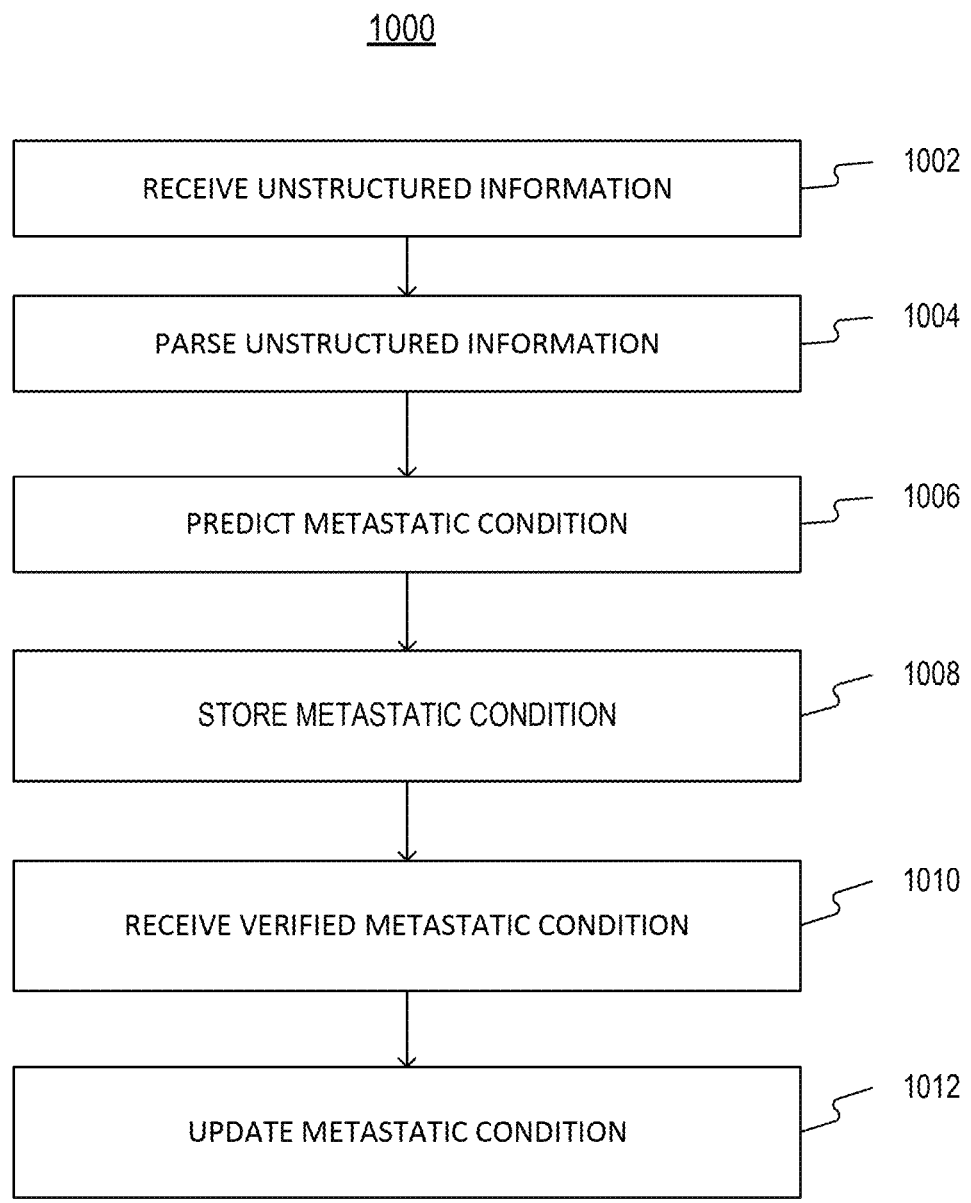
FIG. 10 is a flowchart illustrating an exemplary process for updating metastatic conditions.

FIG. 10 is a flowchart illustrating an exemplary process 1000 for updating metastatic conditions, consistent with the present disclosure. While process 1000 is described in connection with computing device 102, one skilled in the art would understand that one or more steps of process 1000 may be performed by other components of the system (e.g., client device 101).

At step 1002, computing device 102 may receive unstructured information. In some embodiments, unstructured information may be part of a scanned document, a handwritten note, an electronically written note, or other medical document. In some embodiments, unstructured information may include medical data associated with the patient (e.g., a metastatic condition, a patient age, a type of disease, a disease stage, etc.).

At step 1004, computing device 102 may parse unstructured information (e.g., unstructured information in a patient document). In some embodiments, parsing unstructured information may include identifying information contained in a document (e.g., identifying a metastatic condition of a patient, identifying a patient name, an admittance date, a line of therapy, a drug, etc.) and/or converting all or a portion of a document to a structured format. By way of example, a document may be an electronic document having structured and/or structured information (e.g., a pdf document, an XML file, etc.), an image, a chart, a drawing, or any other source of medical information. In some embodiments, an electronic document may be generated by a scanning device (e.g., a portable document scanner, a multi-functional printer, etc.), which may be connected to network 104. For example, a scanning device may scan a physical document and generate an electronic (e.g., structured) document including information from the physical document.

In some embodiments, parsing unstructured information may include extracting metastatic information, which may be used to predict a metastatic condition. In some embodiments, extracted metastatic information may be associated with a patient identifier (e.g., linked to an electronic record of a patient identified in a document). In some embodiments, a trained model (e.g., implemented by a computing device 102) may parse unstructured information. A trained model may be, without limitation, any one of a computer software module, an algorithm, a machine-learning model, a data model, a statistical model, a recurrent neural network (RNN) model, a long-short term memory (LSTM) model, or another neural network model, consistent with the disclosed embodiments. A trained model may be implemented at computing device 102 or another computing device connected to network 104. In some embodiments, metastatic information may be identified from structured information (e.g., structured information that is part of a patient dataset).

At step 1006, computing device 102 may predict a metastatic condition, which may include generating a predicted metastatic condition (e.g., a predicted metastatic condition that may be used in process 900) for a patient (e.g., a patient identified in a document, manually identified by a user, etc.). For example, computing device 102 may predict a metastatic condition based on identifying a metastatic condition of a patient (e.g., identifying a metastatic condition of a patient from unstructured information associated with a patient). In some embodiments, computing device 102 may also determine a level of confidence of a predicted metastatic condition. For example, a computing device 102 may determine a level of confidence of a predicted metastatic condition according to a trained model. A level of confidence may be expressed as a percentage (e.g., 90% chance of a patient having a particular metastatic condition), a combination of words (e.g., "likely," "somewhat likely," "very likely," "suspected," etc.), a type of visual indicator (e.g., described with respect to FIGS. 8A-8E), etc. In some embodiments, different levels of confidence may be associated with different expression. Merely by way of example, a phrase of "very likely" may be associated with a level of confidence reaching a threshold of 90% certainty of a particular metastatic condition. In some embodiments, computing device 102 will predict a metastatic condition based on at least two documents.

At step 1008, computing device 102 may store a metastatic condition (e.g., a metastatic condition determined at step 1006). A metastatic condition may be stored locally at computing device 102, database 103, or any storage device connected to network 104.

At step 1010, computing device 102 may receive a verified metastatic condition, which may have been transmitted by a client device 101. In some embodiments, a verified metastatic condition may be transmitted from a client device 101 to a computing device 102 in response to a predicted metastatic condition received by the client device. In some embodiments, a verified metastatic condition may be received in response to a user input at a client device 101 (e.g., a user input of a verified metastatic condition into a user interface, as depicted in exemplary fashion with respect to FIGS. 8C-8E). Alternatively or additionally, a verified metastatic condition may be received in response to a user input (e.g., entry of a stage IV condition) into a data element (e.g., a structured data element of a patient medical record). In some embodiments, computing device 102 may transmit a predicted metastatic condition and/or a verified metastatic condition to a remote device (e.g., database 103, a client device that transmitted a verified condition, a client device separate from a client device transmitting a verified condition, etc.). For example, computer device 102 may transmit a predicted metastatic condition and/or a verified metastatic condition to a mobile device (e.g., mobile phone, laptop, smartwatch, or other portable networked device). In some embodiments, computing device 102 may forgo updating a predicted metastatic condition based on a verified metastatic condition (e.g., a verified metastatic condition indicating that a patient is non-metastatic or metastatic). For example, in response to receiving a verified metastatic condition indicating a patient is metastatic, computing device 102 may cease to extract metastatic information from a received document associated with that patient, may cease to predict a metastatic condition for that patient, and/or may cease to transmit a predicted metastatic condition for that patient.

At step 1012, computing device 102 may update a metastatic condition. In some embodiments, computing device 102 may update a metastatic condition of a patient based on a verified metastatic condition for that patient (e.g., received at a computing device 102 from a client device 101). In some embodiments, updating a metastatic condition may include replacing a metastatic condition stored at a device separate from computing device 102 (e.g., database 103). Updating a metastatic condition may also include changing displayed information. For example, computing device 102 may cause an update to a display of at least one indicator, and the update may be based on a verified metastatic condition of a patient. By way of further example, a computing device 102 may cause a predicted eligibility indicator 825, which may be displayed at a client device 101, to change to a positive eligibility indicator 824 or a negative eligibility indicator 826. In some embodiments, a change in a visual element to be displayed may be based on whether a verified metastatic condition indicates that a patient is metastatic or non-metastatic and/or a criterion of a trial. In some embodiments, computing device 102 may cause a removal of at least one trial from a subset of trials based on a verified metastatic condition of a patient. For example, a computing device 102 may cause a user device 101 to remove an indicator, region, sub-region, interface, etc. from a display. Merely by way of further example, when a computing device 102 determines, such as based on a verified metastatic condition, that a patient does not satisfy a criterion for a trial (e.g., a trial included in sub-region 823), it may cause the unqualified trial to be removed from an interface (e.g., user interface 800, which may be displayed at a client device 101).

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering, repeating, inserting, and/or deleting steps. It is intended, therefore, that the specification and examples be considered as illustrative only, with a true scope and spirit being indicated by the following claims and their full scope of equivalents.

What is claimed is:

1. A system for determining trials using a metastatic condition of a patient, the system comprising:
  at least one processor programmed to:
    receive, via a first user interface, a selection of trial eligibility criteria associated with a plurality of trials;
    generate, based on the selected trial eligibility criteria, code representing a plurality of expression tree algorithms associated with the plurality of trials;
    receive a selection of the patient;
    access, in response to the selection of the patient, a patient dataset associated with the patient;
    receive at least one image of a medical record associated with the patient, wherein the at least one image is captured by a scanning device associated with the at least one processor and uploaded from the scanning device to the at least one processor;
    extract, by a trained recurrent neural network model, unstructured metastatic condition data associated with the patient from the at least one image;
    convert, by the trained recurrent neural network model, the unstructured metastatic condition data to structured metastatic condition data associated with the patient;
    generate, based on the structured metastatic condition data, a predicted metastatic condition for the patient;
    wherein determining the predicted metastatic condition includes application of a trained model configured to receive unstructured information and output the predicted metastatic condition based on the unstructured information;
    cause display of at least a first portion of the patient dataset and the predicted metastatic condition via a second user interface, the second user interface including at least one element for verifying the predicted metastatic condition;
    identify, based on at least a second portion of the patient dataset, the predicted metastatic condition, and the code representing the plurality of expression tree algorithms, an initial subset of trials for which the patient is eligible within the plurality of trials;
    cause display of the initial subset of trials for the patient via the second user interface;
    after causing display of the initial subset of trials for the patient via the second user interface:
      receive, via the second user interface, an input indicating that a user has verified the predicted metastatic condition of the patient thereby providing a verified metastatic condition of the patient, the input received through an interaction of the user with the at least one element for verifying the predicted metastatic condition; and
      in response to receiving the input indicating that the user verified the predicted metastatic condition of the patient, cause display of an updated subset of trials for which the patient is eligible within the plurality of trials based on the verified metastatic condition.

2. The system of claim 1, wherein the predicted metastatic condition comprises a degree of likelihood determined by the trained recurrent neural network model.

3. The system of claim 1, wherein the at least one image is captured by the scanning device from a physical document.

4. The system of claim 1, wherein the patient dataset is stored among a plurality of patient datasets in a database.

5. The system of claim 1, wherein the at least one processor is further programmed to transmit the predicted metastatic condition and the verified metastatic condition to a remote device.

6. The system of claim 5, wherein the remote device includes a mobile device.

7. The system of claim 1, wherein the at least one processor is further programmed to update the predicted metastatic condition.

8. The system of claim 7, wherein:
  the verified metastatic condition indicates that the patient is metastatic; and
  the at least one processor is further programmed to forgo updating the predicted metastatic condition based on the verified metastatic condition.

9. The system of claim 1, wherein:
  at least one trial in the plurality of trials is associated with at least one metastatic condition criterion; and identifying the initial subset of trials comprises comparing the predicted metastatic condition to the at least one metastatic condition criterion.

10. The system of claim 9, wherein:
  the at least one processor is further programmed to determine that the predicted metastatic condition satisfies the at least one metastatic condition criterion based on the comparing; and
  identifying the initial subset of trials comprises including the at least one trial in the initial subset of trials.

11. The system of claim 9, wherein:
  the at least one processor is further programmed to determine that the predicted metastatic condition does not satisfy the at least one metastatic condition criterion based on the comparing; and
  identifying the initial subset of trials comprises excluding the at least one trial from the initial subset of trials.

12. The system of claim 1, wherein causing the display of the initial subset of trials comprises displaying criteria of the initial subset of trials and indicators of a patient qualification status for the criteria.

13. The system of claim 12, wherein the at least one processor is further programmed to cause an update to the display of at least one of the indicators based on the verified metastatic condition.

14. The system of claim 1, wherein causing display of the updated subset of trials comprises removing at least one trial from the initial subset of trials based on the verified metastatic condition.

15. A method for determining trials using a metastatic condition of a patient on a computing device, comprising:
  receiving, via a first user interface, a selection of trial eligibility criteria associated with a plurality of trials;
  generating, based on the selected trial eligibility criteria, code representing a plurality of expression tree algorithms associated with the plurality of trials;
  receiving a selection of the patient;
  accessing, in response to the selection of the patient, a patient dataset associated with the patient;
  receiving at least one image of a medical record associated with the patient, wherein the at least one image is captured by a scanning device associated with the computing device and uploaded from the scanning device to the computing device;

extracting, by a trained recurrent neural network model, unstructured metastatic condition data associated with the patient from the at least one image;

converting, by the trained recurrent neural network model, the unstructured metastatic condition data to structured metastatic condition data associated with the patient;

generating, based on the structured metastatic condition data, determining a predicted metastatic condition for the patient;

causing display of the at least a first portion of the patient dataset and the predicted metastatic condition via a second user interface, the second user interface including at least one element for verifying the predicted metastatic condition;

identifying, based on at least a second portion of the patient dataset, the predicted metastatic condition, and the code representing the plurality of expression tree algorithms, an initial subset of trials for which the patient is eligible within the plurality of trials;

causing display of at least the initial subset of trials via the second user interface;

after causing display of the initial subset of trials for the patient via the second user interface:

receiving, via the second user interface, an input indicating a user has verified the predicted metastatic condition of the patient thereby providing a verified metastatic condition of the patient, the input received through an interaction of the user with the at least one element for verifying the predicted metastatic condition; and in response to receiving the input indicating that the user verified the predicted metastatic condition of the patient, causing display of an updated subset of trials for which the patient is eligible within the plurality of trials based on the verified metastatic condition.

16. A non-transitory computer-readable medium comprising instructions that, when executed by one or more processors, cause the one or more processors to:

receive, via a first user interface, a selection of trial eligibility criteria associated with a plurality of trials;

generate, based on the selected trial eligibility criteria, code representing a plurality of expression tree algorithms associated with the plurality of trials;

receive a selection of the patient;

access, in response to the selection of the patient, a patient dataset associated with the patient;

receive at least one image of a medical record associated with the patient, wherein the at least one image is captured by a scanning device associated with the one or more processors and uploaded from the scanning device to the one or more processors;

extract, by a trained recurrent neural network model, unstructured metastatic condition data associated with the patient from the at least one image;

convert, by the trained recurrent neural network model, the unstructured metastatic condition data to structured metastatic condition data associated with the patient;

generate, based on the structured metastatic condition data, a predicted metastatic condition for the patient;

cause display of at least a first portion of the patient dataset and the predicted metastatic condition via a second user interface, the second user interface including at least one element for verifying the predicted metastatic condition;

identify, based on at least a second portion of the patient dataset, the predicted metastatic condition, and the code representing the plurality of expression tree algorithms, an initial subset of trials for which the patient is eligible within the plurality of trials;

cause display of the initial subset of trials via the second user interface;

after causing display of the initial subset of trials via the second user interface:

receive, via the second user interface, an input indicating that a user has verified the predicted metastatic condition of the patient thereby providing a verified metastatic condition of the patient, the input received through an interaction of the user with the at least one element for verifying the predicted metastatic condition; and in response to receiving the input indicating that the user verified the predicted metastatic condition of the patient, cause display of an updated subset of trials for which the patient is eligible within the plurality of trials based on the verified metastatic condition.

* * * * *